Figure 1:
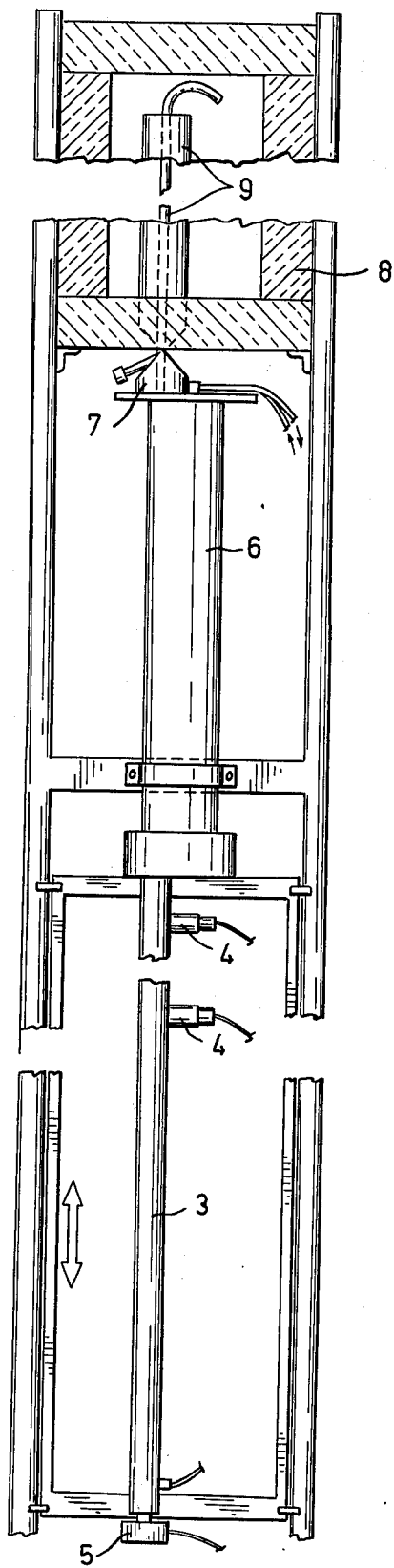

United States Patent [19]

Karinkanta

[11] 3,964,872
[45] June 22, 1976

[54] INJECTING DEVICE OF A SOLVENT-FREE SAMPLE FOR A GAS ANALYZER

[76] Inventor: Hannu Henrik Karinkanta, Linnunpaantie 50, 20840 Turku 84, Finland

[22] Filed: Dec. 27, 1974

[21] Appl. No.: 536,888

[30] Foreign Application Priority Data
Dec. 29, 1973  Finland.................................. 2117/73

[52] U.S. Cl................................... 23/259; 23/253 R; 55/386; 73/422 GC
[51] Int. Cl.².................. G01N 31/06; G01N 31/08; B01D 15/08
[58] Field of Search.................. 23/259, 253 R, 292; 73/422 GC; 55/67, 197, 386

[56] References Cited
UNITED STATES PATENTS

| | | | |
|---|---|---|---|
| 3,205,711 | 9/1965 | Harris................................ | 23/259 X |
| 3,500,617 | 3/1970 | Hall et al............................... | 55/386 |
| 3,536,452 | 10/1970 | Norton et al........................ | 23/259 |
| 3,728,845 | 4/1973 | Haruki et al........................... | 55/67 |

Primary Examiner—Morris O. Wolk
Assistant Examiner—Barry I. Hollander
Attorney, Agent, or Firm—Young & Thompson

[57] ABSTRACT

A sample injecting device for a gas analyzer for injecting solvent-free, non-gaseous samples automatically or manually into the gas analyzer carrier gas, which device essentially comprises a vessel tightly connected to a furnace producing the vaporization or reaction temperature, which vessel is filled with said carrier gas and wherein a higher pressure prevails than in the furnace, a cassette located in the vessel, and exchangeable sample tubes located in the cassette, and means for moving the sample tubes automatically or manually, one at a time and at an adjustable velocity, into said furnace, wherein said carrier gas flushes the sample out from the sample tube, which means thereafter withdraws the sample tube into the cassette.

7 Claims, 3 Drawing Figures

INJECTING DEVICE OF A SOLVENT-FREE SAMPLE FOR A GAS ANALYZER

The injection of substances and components to be analyzed in a qualitative and quantitative chemical analysis into a gas phase, a so called carrier gas, their fractionating in the carrier gas flowing through various columns, and finally the indication and determination of the fractions by using various detectors measuring various properties of gases, is essentially a technique connected with gas-chromatography (GLC). The present invention relates to a sample injecting device, wherein a sample to be analyzed is vaporized by heating it in a furnace, wherefrom a carrier gas, such as e.g. nitrogen, thereafter carries it to a gas analyzer.

In GLC the sample is usually injected as a solution. In certain cases the solvent, however, is undesirable. During the fractionating, the solvent usually is clearly separated from the components to be analyzed and thus hardly hinders the analysis. On the other hand, if the vapour pressure of the substance to be analyzed is close to the vapour pressure of the solvent, its separation from the solvent front may be hard to achieve. Another disadvantage caused by the solvent is a general decline in the sensitivity of the GLC-analysis: the bigger the proportion of the solvent is in the sample, the bigger the initial volume of the sample is after the gasification of the solvent in the injector and the smaller are the concentration maximums of the fractionated components, which the detector detects.

The following devices are available for injecting a solvent-free or solid sample into a GLC carrier gas:

Perkin-Elmer: The sample solution is transferred to an open metal capsule, the solvent is vaporized, and the capsule is closed gas-tight. The sample capsules are put in an injector. The capsules are broken in the hot injector, either one by one at a desired moment, or they will break automatically one after another at set intervals.

Pye Unicam: Resembles the above device.

Barber-Colman: The sample solution is absorbed in a piece of metal net. Upon the evaporation of the solvent the dissolved substance remains in the net. The sample nets are thereafter put in a box, the casing of which is gas-tightly connected to the injector portion, but is located outside its hot zone. The box may be automatically ajusted to change position at desired intervals, whereby each sample net in its turn drops to the hot portion of the injector and the substances absorbed in the nets are flushed into the carrier gas.

Completely different from the above is the new sample injection method using new thin layer chromatography (TLC) technique using tubes, which have a porous layer on their inner surface, according to which method a sample is injected solvent-free in a carrier gas.

The medium of an ordinary TLC is a glass plate, on the surface of which is fastened a 0.25 mm thick porous adsorption layer, usually of silicagel. The sample is adsorbed on the porous surface as a small spot. Thereafter a suitable solvent is absorbed up along the porous surface, whereby the sample components move in the direction of the front of the solvent, each at a velocity determined by its properties. Thus the sample is fractionated into its components.

In some TLC adsorption the absorption layer is spread on the inner surface of a glass or quartz tube. The application and fractionating of the sample on the rising solvent front is done as usual, and a chromatogram tube is obtained. Hereat the occasion, however, arises to connect said chromatogram tube, wherein the solvent first has been evaporated, to part of a closed carrier gas flow system. When the TLC tube connected to the carrier gas flow thereafter is pushed through a heating ring or into a furnace, the fractions of the sample or their decomposition products located on the inner surface of the tube desorb and leave with the carrier gas, and they can be indicated and determined with detectors used in GLC. Various reaction tubes or capsules may be arranged along the carrier gas flow, between the TLC tube and the detector. The arranging of reaction tubes or capsules along the carrier gas flow system is already known from the GLC technique.

Certain disadvantages, however, follow from the fact that the chromatogram tube is part of the closed gas flow:

The exchange of a tube for another is difficult to automatize, and without such an automatization the method is extremely cumbersome which decisively diminishes the value of the method.

The lack of automatization also means that the monitoring of each tube is, in a way, unique so that different analysis results are not fully comparable with one another.

The connectors connecting the tube with the remaining gas system are subject to damage, since the temperatures used are high.

There has not been known a device which would inject a solvent-free sample into a carrier gas flow either as a quick single injection of the entire sample, which kind of injecting method is needed in the GLC technique, or as a slowly advancing scanning injection of the sample, which kind of injecting method is used in the afore-described TLC technique. The present invention thus relates to a device, which makes both these sample injecting methods possible automatically and which, as an auxiliary device, is easy to connect to any gas chromatographic column. The function of the device to be described is thus to get a sample into the gas phase. The monitoring is done by a gas analyzer (comprising one or several detectors, amplifiers, and recorders). The gas analysis technique with its reaction capsules, gas sample valves and columns offers a number of combination possibilities for the final assembly of the system.

The device is primarily characterized in that a gas-tight vessel having an opening big enough for the sample tube to pass, is connected to a furnace producing the vaporization or reaction temperature, which vessel contains a cassette for sample tubes, a sample tube conveyor conveying one sample tube at a time into the furnace and back into the cassette, a mechanism changing the position of the cassette, and a gas pipe or pipe system conducting carrier gas into the vessel. The vessel, which during the run is closed gas-tight, is, however, easy to open for the exchange of the sample tubes of the cassette or the entire cassette. The carrier gas flows through the vessel into the furnace. When the samples tubes move into the furnace or back into the cassette, the carrier gas flows either entirely or partly through this moving sample tube. Thus the gas flow as such drops the pressure in the tube to a lower level than the pressure outside (Bernsulli's general principle concerning fluid flow).

If the sample tube conveyor is part of the inlet gas pipe system for carrier gas and it is fairly gas-tightly connected to the sample tube conveyed by it, the inner gas flows of the vessel and the contamination of the carrier gas eventually caused by them are eliminated. If, on the other hand, there is no need to fear or take into consideration said contamination of the carrier gas, a sufficient quantity of carrier gas flows through the sample tube, even in the event that the sample tube conveyor does not conduct carrier gas, but does not either close the sample tube conveyed by it. It is only essential that the end of a moving sample tube which pushes into the furnace is always free, and the other end of the tube is either free or is more or less loosely connected to the sample tube conveyor depending on the desired construction of the sample tube conveyor. Although it is of no importance as such to the function of the device whether the furnace and vessel are located e.g. parallel or one above the other, the vessel is arranged under the furnace in the embodiment of the device which also the accompanying figures show, whereby easy solutions have been obtained, on one hand for keeping the sample tubes in the cassette, on the other hand for a loose, but sufficiently gas-tight contact between the sample tube and the sample tube conveyor blowing carrier gas; the sample tube simply rests by its own weight on the suitably shaped end of the sample tube conveyor, also on the return of the tube from the furnace into the cassette.

Figure 2:
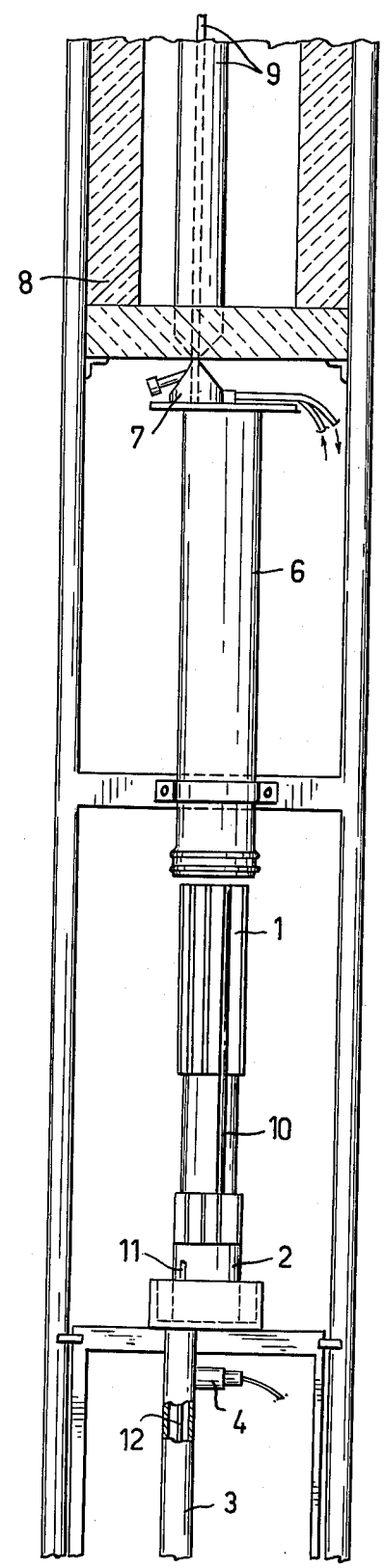
Figure 3:
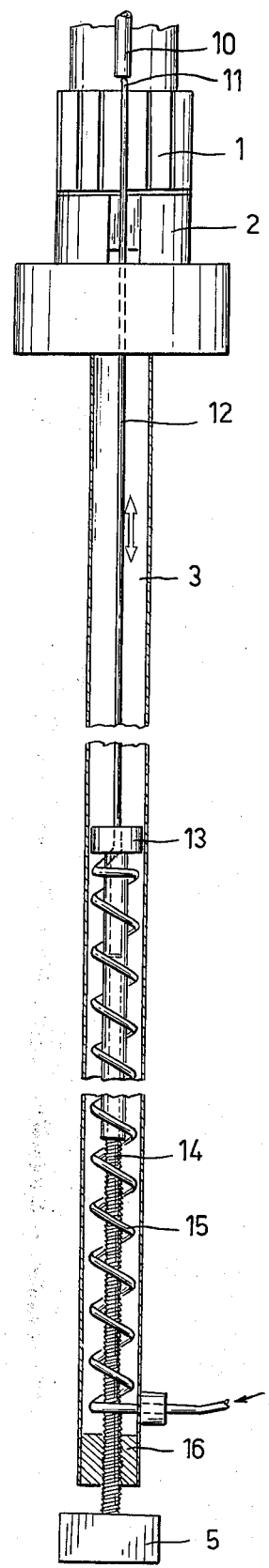

The construction and function of the device in the embodiment shown in the accompanying FIGS. 1, 2 and 3 is as follows:

FIG. 1: Automatic changer and conveyor of a TLC tube in operating position.

FIG. 2: The above opened, filling and emptying position of sample tube cassette.

1. Cassette with grooves or holes on its periphery for the sample tubes.
2. Cassette socket with a mechanism inside it for changing the position of the cassette.
3. Arm with the sample tube conveyor inside it.
4. Limit switches, which give to the sample tube conveyor, when it reaches either extreme position, the opposite moving direction by means of a motor, gears, a long screw and a relay.
5. Motor and gears.
6. Cylindrical casing of the cassette with packing rings in its lower edge.
7. Mantle to be cooled with tap water, with the opening of a tubular furnace inside it. An injector is also here. The injector may be used for testing the function of the gas chromatographic column, eventually also for the standardization of the TLC analysis.
8. Mantle to be heated to a high temperature with the tubular furnace inside it. Between these two mantles (7 and 8), the temperature of the tubular furnace changes sharply over a short distance.
9. Tubular furnace, wherein the sample tubes fit one after another.
10. TLC tube in its groove.

FIG. 3: Sample conveyor of the automatic sample changer.

11. Conical head of sample conveyor, partly penetrated into sample tube. The tube is rising into the oven or returning therefrom.
12. The sample conveyor is a narrow metal tube, which together with an elastic tube spiral 15 guides the moving gas through the sample tube 10 into the furnace 9.
13. Slide, which at the same time prevents the sample tube conveyor from rotating around its longitudinal axis.
14. Long screw.
15. Elastic tube spiral. The carrier gas arrives hereto gas-tightly from the outside of the arm 3.
16. Gas-tight bearing of the long screw 14.

The carrier gas flows along the elastic spiral tube 15 to the rigid tubular sample tube conveyor 12, through the head of which it gets into the free inner space of the vessel. The only possible outlet way for the carrier gas, when the vessel is closed, goes through the tubular furnace 9. When the sample tube conveyor is moving upward, it takes on its head from the cassette 1 a nearby sample tube, pushes it into the tubular furnace and withdraws it into the cassette to its earlier location. The cassette changes position, and the sample tube conveyor starts to carry the next sample tube. In this way, one tube after another goes in the furnace, until the device is stopped. The carrier gas always flows only through a moving sample tube. The adjustment of the velocity of the sample tube depends on each particular purpose of use of the injecting device, e.g. as follows:

In a typical TLC monitoring, the tubes are allowed to move into the oven and back into the cassette at a constant velocity and automatically one after another.

When using the injecting device for the injection of solvent-free samples in the GLC technic, the samples are eluated in the sample tubes, one in each tube, to sharp-edged zones. Hereat the sample tubes must go in the furnace quicker than above and at desired intervals, the length of the intervals depending on the time required by the GLC analysis.

When GLC analyses are required from various points of the same sample tube, the motion of the sample tube must be stopped after each injection for the time of the corresponding GLC analysis.

What I claim is:
1. A sample injecting device for a gas analyzer, comprising a vessel, a cassette within said vessel, a plurality of straight elongated sample tubes open at both ends disposed in said cassette in parallel relation to each other, a furnace with which said vessel communicates, and means for conveying said sample tubes one by one lengthwise from said cassette into said furnace and for returning said sample tubes from said furnace to said cassette, said conveying means comprising an elongated conduit paralle to said sample tubes and selectively engageable with one of said open ends of a said sample tube, means for moving said elongated conduit lengthwise to introduce said sample tube into said furnace and to withdraw said sample tube from said furnace, and means to introduce a carrier gas through said elongated conduit and through said sample tube.

2. A device as claimed in claim 1, said moving means comprising an elongated screw, and means for rotating said screw in opposite directions thereby to advance and retract said conduit and tube.

3. A device as claimed in claim 2, said introducing means comprising a flexible conduit wound helically about at least a portion of said screw.

4. A device as claimed in claim 1, said furnace and cassette and vessel and tubes and conduit being vertically disposed with said furnace above said vessel and said vessel above said conduit, the lower end of the tube in said furnace resting by gravity on the upper end of said conduit.

5. A device as claimed in claim 4, said moving means comprising motor means for raising said conduit at a controlled rate of speed thereby progressively to introduce said tube into said furnace.

6. A device as claimed in claim 1, and means to rotate said cassette about an axis parallel to said tubes thereby successively to position said tubes one by one in alignment with said conduit.

7. A device as claimed in claim 6, said axis being vertical.

* * * * *